United States Patent [19]
Alpern et al.

[11] Patent Number: 5,320,528
[45] Date of Patent: * Jun. 14, 1994

[54] DENTAL ARTICULATOR

[76] Inventors: Michael C. Alpern, 551 Port Charlotte Blvd., Port Charlotte, Fla. 33952; Ralph J. Brandon, 302 Nesbit St., Punta Gorda, Fla. 33950; Douglas G. Nuelle, 2595 Harbor Blvd. Suite 102, Port Charlotte, Fla. 33952

[*] Notice: The portion of the term of this patent subsequent to Nov. 3, 2009 has been disclaimed.

[21] Appl. No.: 939,001

[22] Filed: Sep. 2, 1992

Related U.S. Application Data

[63] Continuation-in-part of Ser. No. 650,874, Feb. 5, 1991, Pat. No. 5,160,262.

[51] Int. Cl.$^5$ ............................................. A61C 11/00
[52] U.S. Cl. ........................................ 433/58; 433/57; 433/59; 433/62
[58] Field of Search ................. 433/55, 57, 58, 59, 433/60, 61, 62, 63, 64, 65, 56

[56] References Cited

U.S. PATENT DOCUMENTS

| | | | |
|---|---|---|---|
| D. 261,805 | 11/1981 | Edwardson | D24/10 |
| 1,022,055 | 4/1912 | Weiss | 433/64 |
| 1,670,311 | 5/1928 | Musante | 433/55 |
| 1,989,367 | 1/1935 | Keeney | 433/58 |
| 2,617,195 | 11/1952 | Perkell et al. | 433/65 |
| 3,159,915 | 11/1962 | Beu et al. | 433/57 |
| 3,423,834 | 1/1969 | Irish | 433/59 |
| 3,908,271 | 9/1975 | Derda et al. | 433/58 |
| 4,024,640 | 5/1977 | Guichet | 433/59 |
| 4,047,302 | 9/1977 | Cheythey | 433/56 |
| 4,233,850 | 11/1980 | Edwardson | 433/56 |
| 4,245,987 | 1/1981 | Bertoldi | 433/61 |
| 4,290,754 | 9/1981 | Edwardson | 433/56 |
| 4,439,150 | 3/1984 | Edwardson | 433/56 |
| 4,453,918 | 6/1984 | Edwardson | 433/55 |
| 4,496,319 | 1/1985 | Steinbock | 433/57 |
| 4,496,320 | 1/1985 | Hwang et al. | 433/60 |
| 4,505,674 | 3/1985 | Edwardson | 433/59 |
| 4,541,807 | 9/1985 | Rolfs | 434/264 |
| 4,695,252 | 9/1987 | Edwardson | 433/73 |
| 4,715,814 | 12/1987 | Kaoru et al. | 433/59 |
| 4,758,155 | 7/1988 | Marino | 433/61 |

*Primary Examiner*—John J. Wilson
*Attorney, Agent, or Firm*—Wood, Herron & Evans

[57] ABSTRACT

A dental articulator having an upper support member for supporting a dental cast and a lower support member for supporting a second dental cast. A polycentric hinge joint is provided for simulating the temporomandibular joint of a patient. The polycentric hinge joint comprises a fossae block secured to the upper support member and a condyle member secured to the lower support member which engages a fossae recess in the fossae block. A spring is provided for securing the lower support member to the upper support member and simulating the muscles used for mastication. A pair of wires are provided for simulating the ligaments of a patient. The upper end of each wire passes through an opening in the upper support member. The lower end of each wire is secured to the lower support member. A limiting block is provided on the upper end of each of the wires so as to restrict its movement. Removable adjustment post assemblies are provided at the forward end and rear end of the articulator so that the upper and lower support members may be spaced apart a desired distance.

8 Claims, 15 Drawing Sheets

DENTAL ARTICULATOR

RELATED APPLICATION

This application is a continuation-in-part of U.S. patent application Ser. No. 07/650,874, filed Feb. 5, 1991, now U.S. Pat. No. 5,160,262.

FIELD OF THE INVENTION

The present invention relates to dental articulators for use in making dental casts or orthodontic models and for the correction of occlusion of natural dentition. A dental articulator according to the present invention is designed to produce accurate replication of the various movements of the patient's lower jaw with respect to the temporomandibular joint, thus allowing for the replication of the patient's teeth and the effect on the temporomandibular joint under various conditions.

BACKGROUND OF THE INVENTION

Typical prior art dental articulators comprise an upper principal member and a lower principal member which simulate the temporomandibular condylar joint through the use of balls, associated with either the upper or lower principal member, which are received in a slot in the opposing principal member. However, these articulators involve certain compromises from the standpoint of actual kinetics of the relative movements of the mandible relative to the maxilla. Due to the ball and slot arrangement of prior art articulators, the devices are unable to take into consideration the actual configurations of the temporomandibular joint of the patient. Additionally, prior art articulators do not take into account the forces provided by the ligaments and/or muscles of the jaw. Prior art articulators also fail to take into account the actual movement of the lower jaw as the teeth on the maxilla are moved which is in contrast to the actual movement of the mandible of the patient.

Applicants have invented a novel and improved articulator which closely replicates actual human jaw movement and takes into consideration the actual forces applied by the muscles and ligaments in the jaw. Additionally, an articulator made in accordance with the present invention has the ability to take into account variations in the actual configuration of the condyle and fossae of the patient. The present invention also provides means for allowing easy viewing of the lower dental prosthetic and manipulation of the lower jaw member.

SUMMARY OF THE INVENTION

In one aspect of the present invention there is provided a dental articulator having an upper support member for supporting a first dental cast and a lower support member for supporting a second dental cast. A polycentric hinge joint is provided for simulating the temporomandibular condylar joint and for securing the lower support member to the upper support member. The polycentric hinge joint comprises a pair of axially spaced fossae blocks secured to the upper support members. Each block has a fossae recess designed to receive a condyle secured to the lower support member. Means are provided for adjusting the polycentric hinge joint in accordance to a particular patient. Means are provided for securing the lower support member to the upper support member and for simulating the muscles used for mastication.

In another aspect of the present invention there is provided a dental articulator having an upper support member for supporting a first dental cast and a lower support member for supporting a second dental cast. Joint means are provided for securing the lower support member to the upper support member and for simulating the temporomandibular condylar joint. Means are provided for positioning the lower support member with respect to the upper support member at a desired position which comprises a first removable post assembly located at the forward end of the articulator and at least one removable post assembly located at the rear end of the articulator. Means are provided for mounting and dismounting the post assembly from the upper support member.

In yet another aspect of the present invention there is provided a dental articulator having an upper support member for supporting a first dental cast and a lower support member for supporting a second dental cast. Joint means are provided for securing the lower support member to the upper support member and for simulating the temporomandibular condylar joint. The articulator further includes a neck portion secured at the rear end of the upper support member and a base portion secured at the lower end of the neck portion. Means are also provided so that the neck portion can be readily disconnected from said base portion.

DETAILED DESCRIPTION OF THE INVENTION

Figure 1:
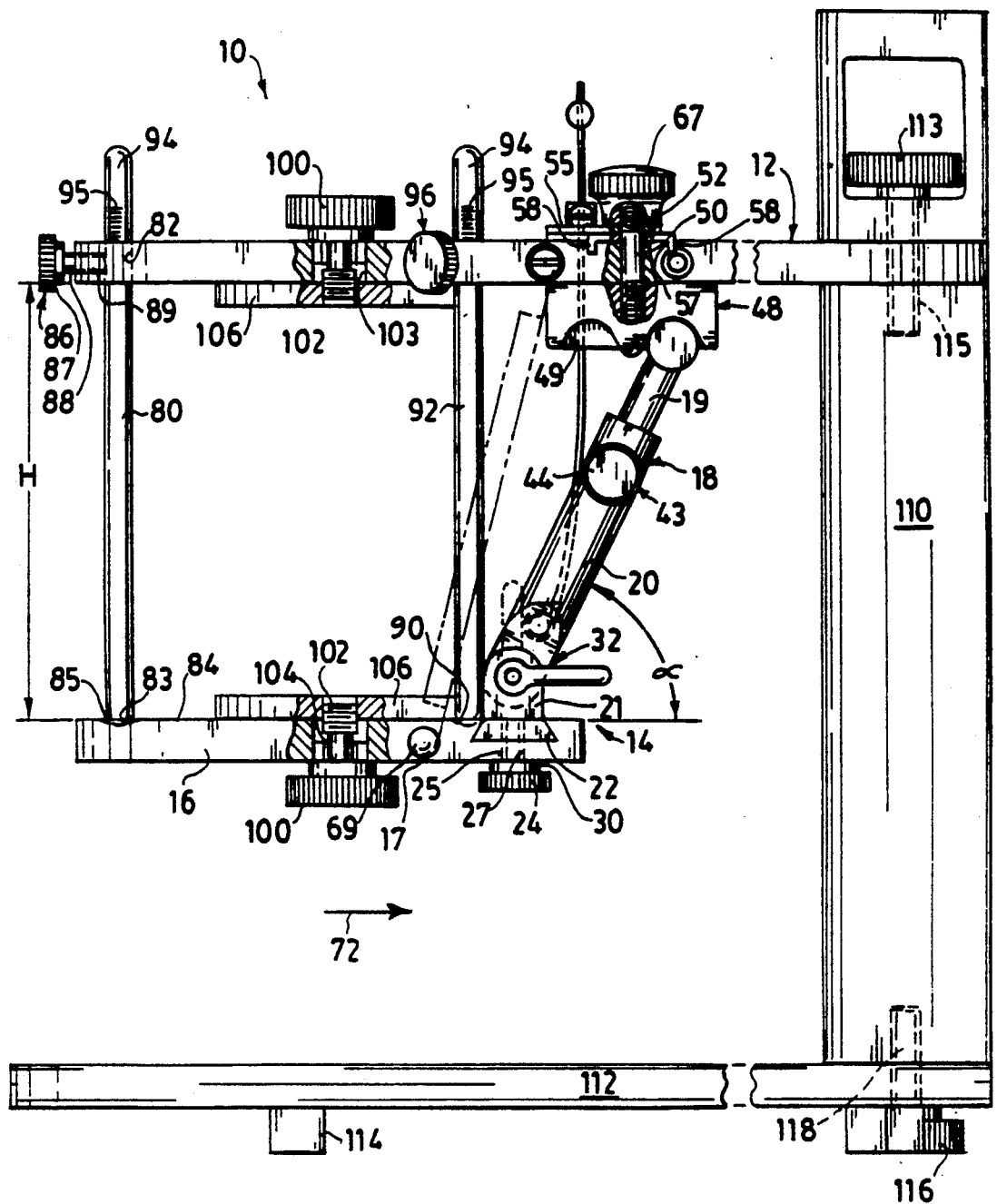
FIG. 1 is a side elevational view of an articulator made in accordance with the present invention.
Figure 2:
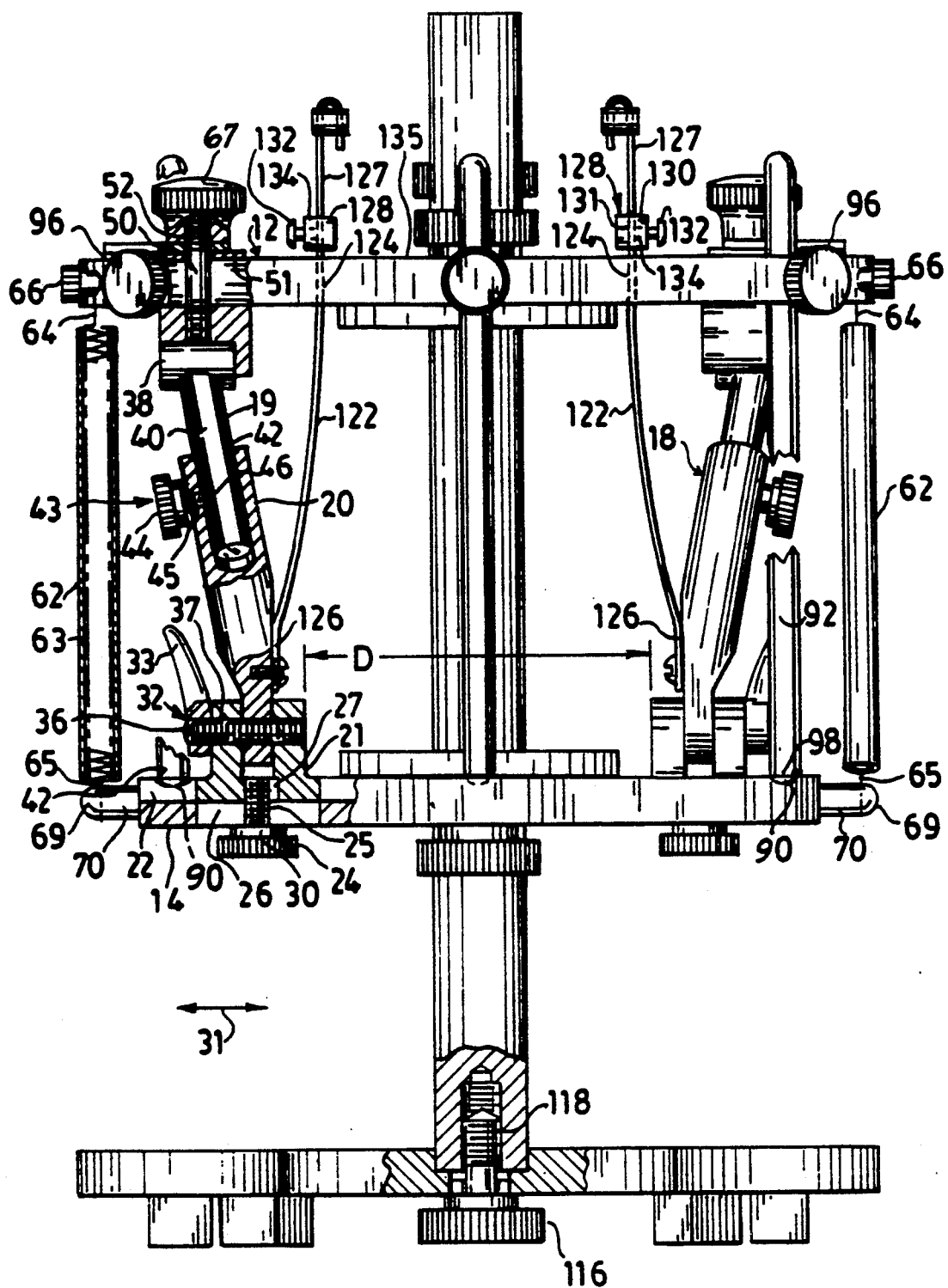
FIG. 2 is a front elevational view, partially broken away, of the articulator of FIG. 1.
Figure 3:
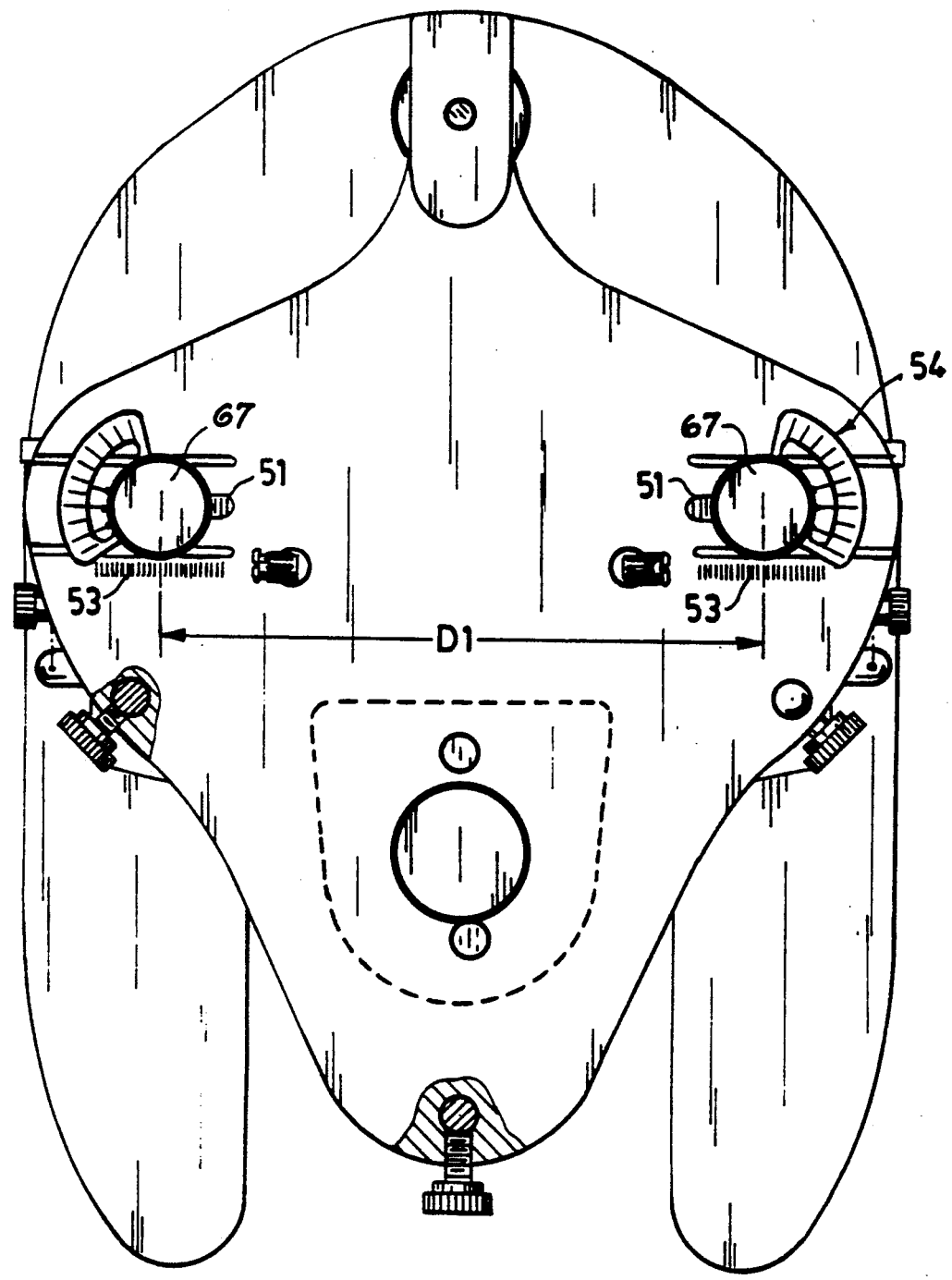
FIG. 3 is a top plan view of the articulator of FIG. 2.

Referring to FIGS. 1-4 there is illustrated a dental articular 10 made in accordance with the present invention which is typically used for the supporting of dental casts or orthodontic models. The articulator 10 includes an upper support member 12 supporting a first dental cast 13 and a lower support member 14 supporting a second dental cast 15. FIGS. 1 and 2 omit illustrating the dental casts 13, 15 for the sake of clarity. The lower support member 14 comprises a base member 16 which supports the second dental cast 15 and a pair of axially spaced condyle support members 18. In the particular embodiment illustrated, each condyle support member 18 includes a condyle 19, a central support section 20 and lower mounting end 21. The lower mounting end 21 of each condyle support member is slidably mounted to base member 16.

In the embodiment illustrated, lower mounting end 21 is designed to slide within an axially-extending slot 22 in base member 16. Associated with each lower mounting end 21 is a hand tightening mean for securing mounting member 21 to base member 16 which includes a knob 24 having a threaded shaft 25 designed to pass through an axial extending slot 26 in base member 16 and engage a threaded opening 27 in lower end 21. As knob 24 is turned so that the threads of shaft 25 engage the threads of opening 27, the shank 30 of shaft 25 will press against the lower surface 17 of base member 16 so as to lock lower mounting end 21 in position. To move lower mounting end 21, knob 24 is simply rotated in the opposite direction so that lower mounting end 21 can slide in slot 22. As illustrated in FIG. 1, slot 22 has a dovetail cross sectional shape designed to receive a corresponding mating configuration in the lower mounting end 21 of condyle support member 18 so as to prevent vertical movement therebetween. Therefore, the condyle support member 18 may freely slide in the axial direction indicated by arrows 31, thus, allowing the two condyle support members to be spaced axially apart a distance D as desired by the user.

In the embodiment illustrated, means are provided for adjusting the angle of condyle support member 18 with respect to the base member 16. In the particular embodiment illustrated, this is accomplished by a locking joint 32 which rotatably connects central support section 20 to lower mounting end 21. Locking joint 32 includes a lever 33 having a shaft 36 which passes through aligned opening 37,39 in lower mounting end 21 and central support section 20. When lever 33 is rotated 90° it will either lock or unlock the central support section 20 and lower end so as to allow orientation of the base member 16 to any desired angle $\alpha$. It is, of course, understood that means for adjusting the angle of orientation of condyle support member 18 may be varied as desired, the illustrated locking joint being but one example. As discussed and illustrated later herein, the condyle support member 18 need not be provided with any adjustable means.

Each condyle 19 is slidably mounted to its associate central support section 20. Referring to FIGS. 1, 2, 4-8A and 8B, each condyle 19 comprises an upper engaging section 38 and mounting section 40 extending therefrom. In this embodiment illustrated mounting section 40 comprises of a cylindrical shaft which is designed to slide within an opening 42 in the central support section 18. Mounting section 40 is adjustably positioned within opening 42 by locking means 43. Locking means 43 comprises a knob 44 which has a threaded shaft 45 secured thereto which engages a threaded opening 46 in central support section 20 which communicates with opening 42. By turning knob 44 in the opposite direction, the threaded shaft 45 will bear against mounting section 40 so as to secure condyle 19 in the desired position. By turning knob 44 in the opposite direction, condyle 19 will be released allowing repositioning or removal from central support section 20. Upper engaging section 38 has an outer engaging surface 47 designed to engage a fossae recess 41 in its associated fossae block member 48 which is secured to upper support member 12. A forward capture recess 49 is provided in fossae block member 48 to capture and receive engaging section 38 in the event that engaging section 38 comes out of its associated fossae recess 41. The area between the fossae recess 41 and capture recess 49 simulates the superior eminence of the temporomandibular joint.

The fossae block members 48 are each slidably mounted with respect to upper support member 12 such that the axial distance D1 therebetween may be varied as desired. In the particular embodiment illustrated, each fossae block member 48 is axially adjustable through the use of knob 67. A threaded shaft member 50 is secured to fossae block member 48 and passes through a respective axial extending slot 51 formed in upper support member 12. The threaded shaft member 50 is designed to engage a threaded opening 52 in its associated knob 49. By tightening or loosening knob 67 the fossae block member 48 will either be tightened or loosened with respect to the upper support member 12, thus allowing axial positioning/spacing of the fossae block members 48 to the desired distance to match the anatomical conditions of the patient for which the articulator is being used. Such anatomical measurement, may for example, be obtained through the use of tomography as is well known in the art. Axial Tome Corporation produces and sells a suitable device for obtaining the desired anatomical measurements. Adjacent each knob 67 there is provided a lineal scale 53 (FIG. 3) so that the axial spacing of fossae block members 48 may be easily and conveniently determined by appropriate readings therefrom. In addition, an angular scale 54 is provided for setting the angle orientation of a fossae block member 48 as desired. Angular scale 54 comprises a plate 55 having a opening 56 designed to receive the shaft 50. Shaft 50 is designed to receive plate 55 such that it represents the angular position of fossae block member 48. A second plate 57 is provided which has a pair of downwardly extending projections 58 which engage a corresponding groove 59 in upper support member 12. The plates 55,57 each have respective angular markings so that the angular position of fossae block member 48 can be accurately positioned to correspond to the anatomical condition of the patient.

Each fossae block member 48 and its associated condyle 19 cooperate so as to provide a polycentric hinge joint which simulates the temporomandibular condylar joint of an individual. Preferably, the fossae block members 48 are made of an appropriate high molecular weight plastic material to simulate the movement in a human jaw. Examples of suitable plastic materials are polyethylene and polypropylene, however, any suitable material may be used.

Figure 4:
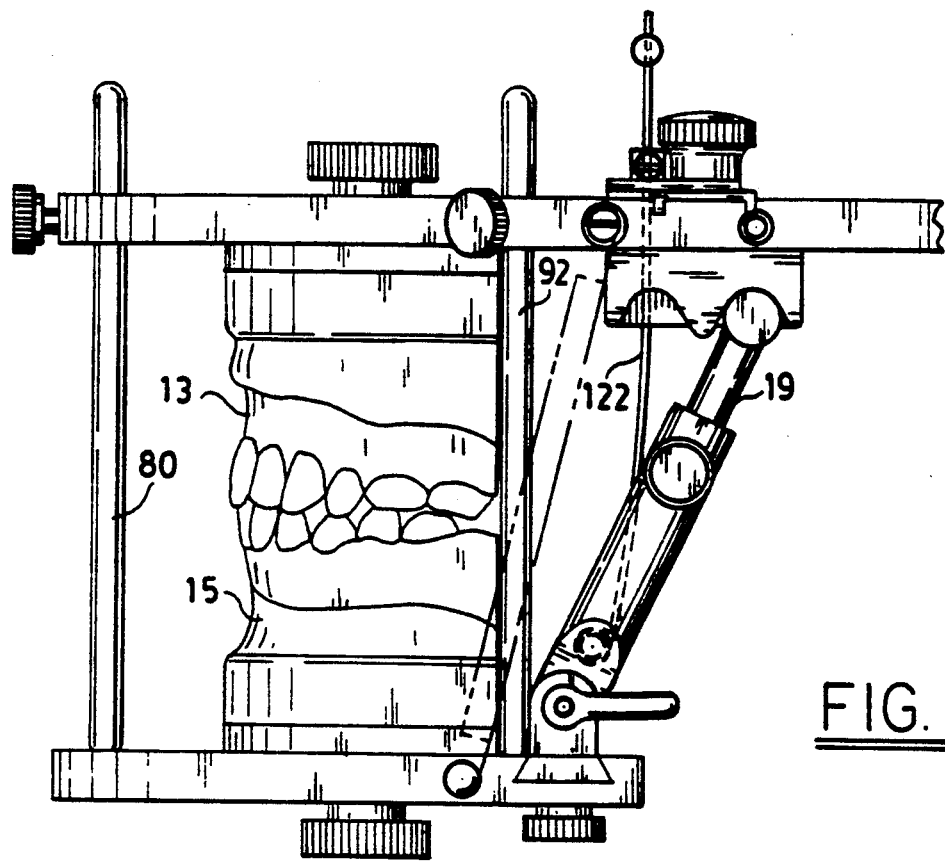
FIG. 4 is a partial view of the articulator of FIG. 1 illustrating a dental cast mounted to the upper and lower support members.

A pair of coil springs 62 are provided for securing upper support member 12 to lower support member 14 and for simulating the muscles used for mastication between the upper and lower teeth of an individual. In the embodiment illustrated, a cylindrical protective plastic sheath 63 surrounds each coil spring 62. The coil springs 62 each have an upper end 64 which is secured to upper support member 12 and a lower end 65 designed to be secured to lower support member 14. In the particular embodiment illustrated, the upper end 64 is secured to upper support member 16 by a threaded member 66 which clampingly secures the upper end 64 of coil spring 62 to upper supporting member 12. It is to be understood that the upper end 64 of the coil springs 62 may be secured in any desired fashion to upper support member 12. In the particular embodiment, the lower end 65 of each spring 62 is provided with a circular loop 69 designed to receive a pin 70 secured to base member 16. The pin 70 allows lower end 65 of spring to be easily mounted and removed therefrom and also allows it to freely rotate as lower support member 14 is moved, as is discussed later herein. The coil springs 62 bias the lower support member 14 toward the support member 12. Additionally, by properly locating the position at which the upper and lower ends 64,65 are secured to upper support and lower support members 12,14, respectively, the lower support member 14 is also biased toward the rear lateral section of articulator 10 as illustrated by arrow 72 in FIG. I. The coil springs 62 are designed to provide a sufficient amount of force such that any dental cast or orthodontic model that is placed on lower support member 14 will be adequately supported yet be of sufficient resiliency so that the position of the lower support member 14 may be easily manipulated by the user. In the particular embodiment illustrated each coil spring 62 is made of a stainless steel wire having a diameter of 0.030 inches (0.762 mm) and has an outside cross sectional diameter of 0.210 inches (5.33 mm) providing an initial loading of about 3 lbs. when the articulator is in the closed position as illustrated in FIG. 4. Spring 62 also has a spring constant of about 3½lbs./inches. It is of course understood that each spring 62 may be designed to provide the desired physical character desired.

Articulator 10 is also provided with means for positioning the lower support member 14 at a desired distance H with respect to said upper support member 12. This is accomplished by providing a forward removable adjustment rod 80 which passes through an opening 82 in upper support member 12. The lower end 83 of rod 80 is designed to engage the top surface 84 of base member 16. Preferably as illustrated, a recess 85 is formed in base member 16 so as to properly locate and position the lower support member 14 with respect to the upper support member 12. Locking means 86 is provided for moving rod 80 to the desired position and locking rod 82 at such desired position. In the particular embodiment illustrated, locking means 86 comprises a knob 87 having threaded shaft 88 designed to engage a threaded opening 89 which communicate with opening 82. Opening 89 allows threaded shaft 88 to pass therethrough until it engages rod 80. By appropriately tightening or loosening knob 87, rod 80 can be easily adjusted to provide the desired vertical distance H between upper support member 12 and lower support member 14.

In a similar manner, a pair of axially spaced rear lateral adjustment rods 92 are also provided. The rear lateral adjustment rods 92 each extend through a respective opening 94 in the rear lateral section of upper support member 12. Locking means 96 are provided for adjusting the vertical position of rear lateral adjustment rods 92 in the same manner as locking means 86 was used to lock forward rod 80, like numerals representing like parts. Lower end 98 of rear lateral adjustment rods 92 are designed to engage and mate with the base member 16 of lower support member 14. As with forward rod 80, rear lateral adjustment rods 92 are preferably designed to mate in a dished recess 90 formed in base member 16 While adjustment rods 80 and 92 may all be used at the same time generally the front adjustment rods 80 are initially used to set up the dental casts to be mounted to the articulator 10. Once the dental casts have been mounted, the rear lateral adjustment rods 92 are positioned at the prepositioned height, forward adjustment rod 80 may be removed. This allows the user to have free access to the prosthetic devices. Preferably, as illustrated, the upper ends 94 of rods 80,92 are provided with an appropriate scale 95 such that the vertical displacement between the lower support member 14 and upper support member 12 can be accurately maintained or redefined at some later time should the need arise.

As is customary with articulators of the prior art, articulator 10 is appropriately provided with means for securing dental casts thereto. Thus, the upper support member 12 and lower support member 14 are each provided with a mounting knob 100 having a threaded shaft 102 designed to pass through opening 103, 104 in upper and lower members 12,14, respectively, and engage a mounting plate 106 upon which the appropriate dental casts or orthodontic models may be secured. Typically, as illustrated in FIG. 4, casts of the upper and lower teeth of a patient are mounted to upper support member 12 and lower support member 14, respectively. It is to be understood and appreciated that the means for securing the dental casts or orthodontic models may be varied as desired.

The upper support member 12 is secured to neck portion 110 which is in turn secured to a base 112 which allows the articulators to be placed on the desired work surface. In the embodiment illustrated upper support member 12 is secured to neck portion 110 by a knob 113 having a threaded shaft 115 which passes through an opening in upper support member 12 and engages a threaded opening in neck portion 110. However, upper support member 12 may be secured to neck portion 110 in any desired manner. The base 112 is provided with a plurality of feet 114 such that the base 112 is spaced slightly from the table or bench upon which the articulator 10 is placed. It is to be understood that the configuration of base 112 and the number and design of feet 114 may be varied as desired. Preferably, as illustrated (FIG. 1), the neck portion 110 is releasably secured to base 112 such that the neck portion 110 may be used to lift the upper and lower members 12,14 with their appropriate dental cast devices thereon and manipulated by the user as desired. This allows the user to view the dental cast at any appropriate angle. The neck portion 110 in the particular embodiment illustrated is releasably mounted to base 112 through the use of a threaded knob 116 having a threaded shaft 118 which engages a threaded opening 120 in the bottom of neck portion 110. It is to be understood that the neck portion 110 may be releasably mounted to the base in any desired manner, the illustrated embodiment being only one means by which this may be accomplished.

The articulator is also provided with means for simulating the ligament of a jaw, in particular, the stylo-mandibular and spheno-mandibular ligaments in the mouth. This is accomplished through the use of a pair of wires 122 (or any other suitable flexible connecting elements) which pass through respective openings 124 in the upper support member 12. Each of these wires 122 is designed to simulate the ligaments on either side of the patient's jaw. In the particular embodiment illustrated each wire 122 is made of a spring type metal. The lower end 126 of wire 122 is secured to the lower end of central support section 20. The opening 124 is sized so as to allow the wire 122 to freely move therethrough. At the upper end 127 of each wire 122 above upper support member 12 there is provided a locking means 128 designed to restrict the amount of movement of the wire 122. In the particular embodiment illustrated means 128 comprises a block 130 having an opening 131 designed to allow the upper end of wires 127 to freely pass therethrough. A screw 132 is provided which passes through an appropriate threaded opening 134 in each block 130 such that the screw 132 engages the wire 122. The screw 132 is designed such that when tightened against wire 122, the screw 132 will permanently position the block 130 at any desired location. By determining the position of block 130 with respect to the upper surface 135 of upper support member 12, this will restrict the overall movement of the lower support member 14 with respect to the upper support member 12. If the lower support member 14 is moved too far, the block member 130 will engage the upper surface 135 of upper support member 12 thus restricting any further movement along an arc which is determined by the length of the wire 122 between the block 130 and condyle. By taking appropriate measurements from the patient, the amount of movement can be restricted as desired by the user.

Figure 5:
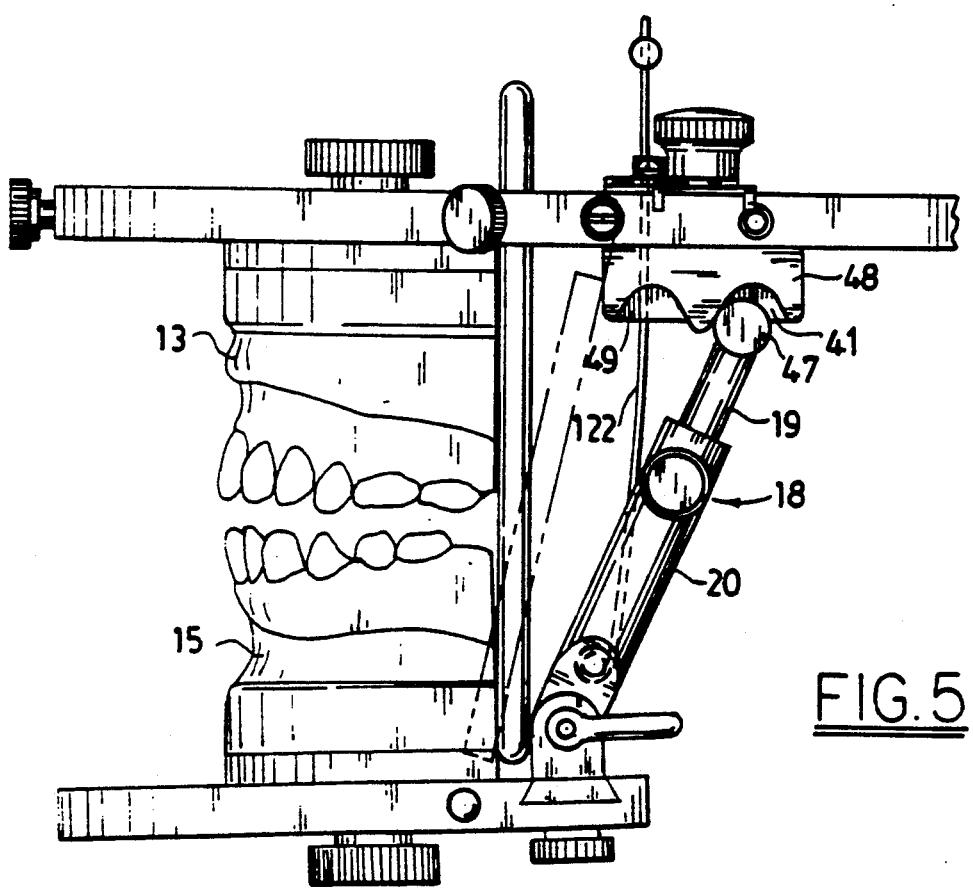
FIG. 5 is a view similar to FIG. 4 illustrating the articulator in a first partially open position.
Figure 6:
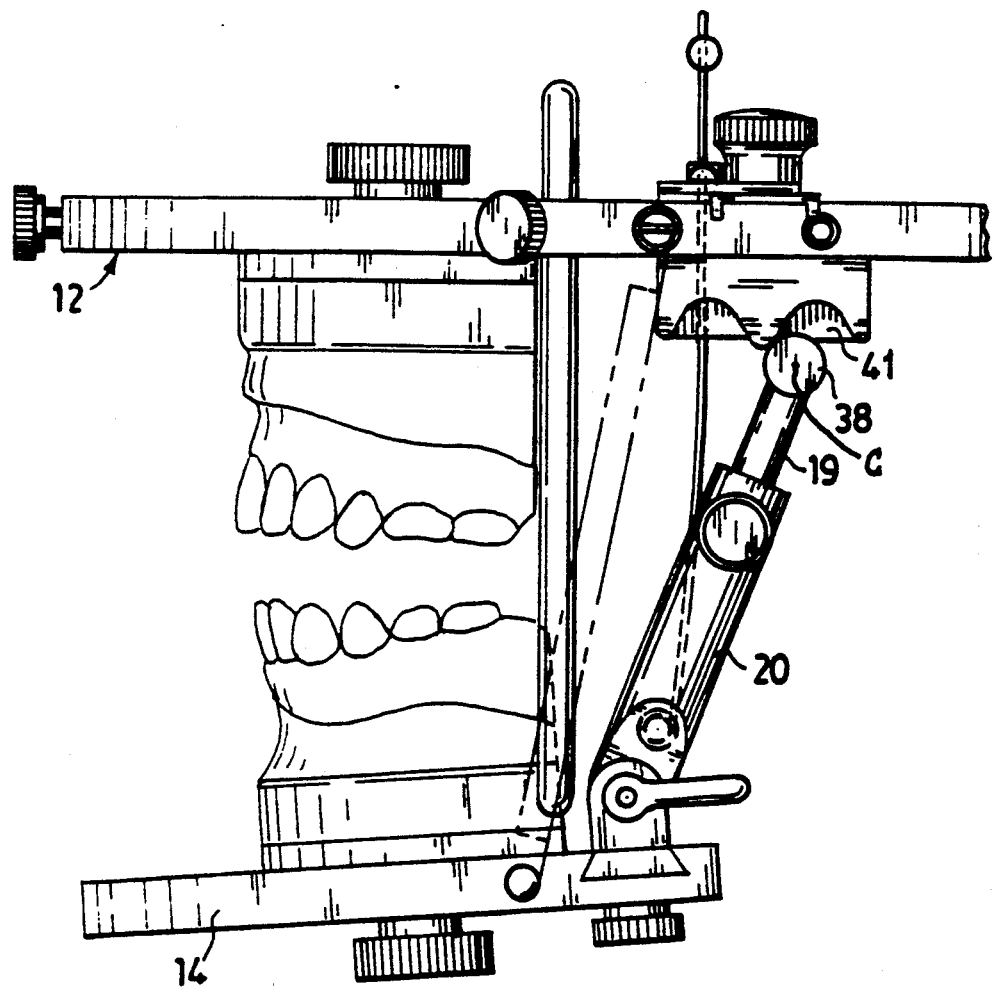
FIG. 6 is a view similar to FIG. 4 illustrating the lower support member being moved in a second fully opened position.
Figure 7:
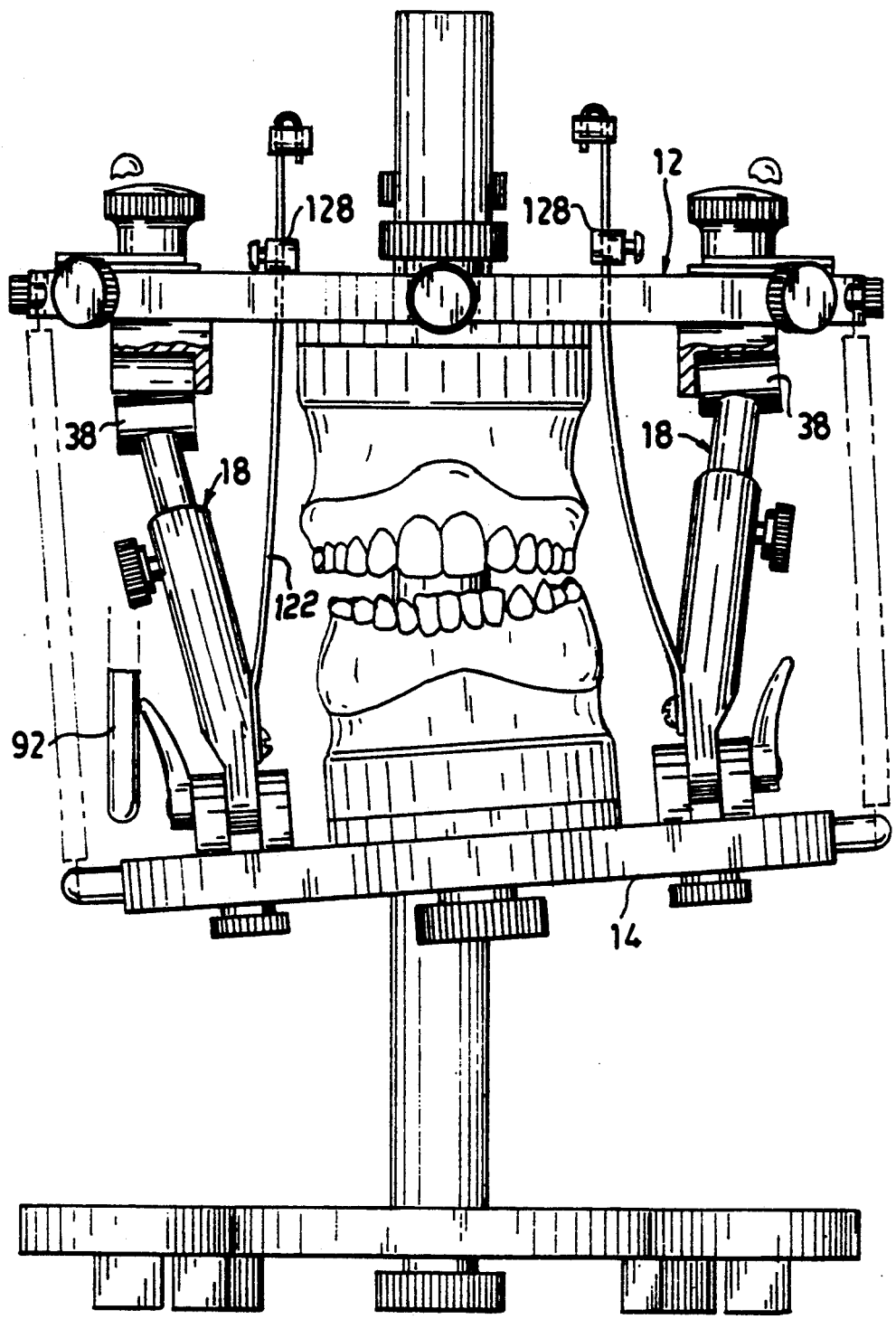
FIG. 7 is a front elevational view similar to FIG. 2 illustrating a dental cast mounted thereon and the articulator moved to simulate lateral movement of the jaw.
Figure 8A:
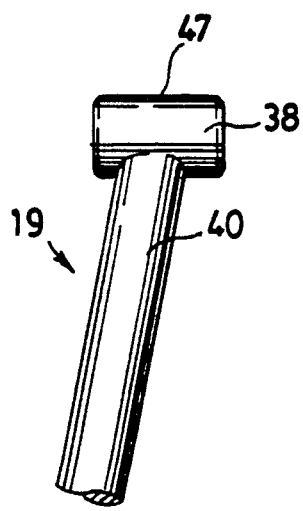
FIG. 8A is a front elevational view of a condyle member used in an articulator of the present invention.
Figure 8B:
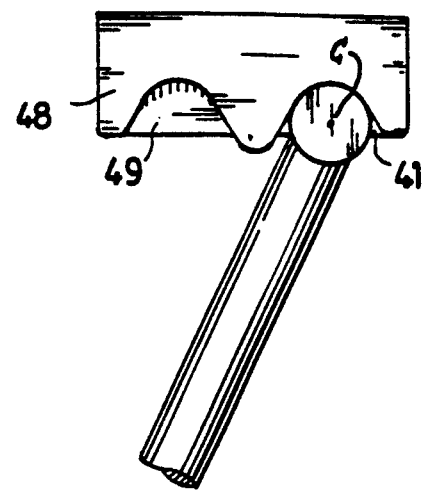
FIG. 8B is a side elevational view of the condyle of FIG. 8A as placed in its respective fossae block member when the articulator is in the closed position as illustrated in FIG. 4.
Figure 8C:
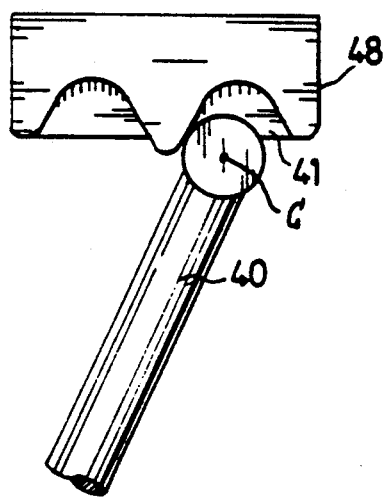
FIG. 8C is an enlarged side elevational view of the condyle of FIG. 8B illustrating the condyle wherein the articulator is in the first partially opened position as illustrated in FIG. 5.
Figure 8D:
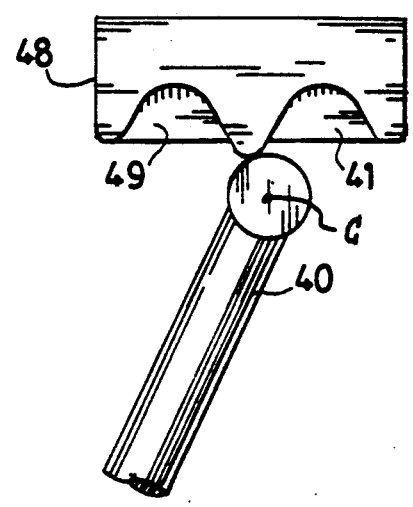
FIG. 8D is an enlarged side elevational view of the condyle of FIG. 8B wherein the articulator is in the second fully opened position as illustrated in FIG. 6.

In order to more fully appreciate the advantages of the present invention, the operation of the articulator 10 will now briefly be described. As illustrated in FIG. 4, dental prosthetic devices are mounted to the upper and lower support members 12,14. Adjustment rod 80 is moved to the desired location and secured in position so as to provide the desired vertical distance H between the upper and lower support members 12,14. Once this has been done, the rear lateral adjustment rods 92 may be placed in position and secured. Thereafter, forward adjustment rod 80 may be removed entirely if so desired. The lower support member 14 may be moved freely, for example, as illustrated in FIGS. 5, 6, 7 so as to separate the lower dental cast from the upper dental cast. Since the condyle 19 is not permanently affixed to the fossae block member 48 the condyle 19 is allowed to freely move within the fossae recess 41. As illustrated in FIGS. 6 and 8B-D, the condyle is free to move downward and axially inward much in the same way the condyle of an actual jaw moves in a human being. As can be seen, the center C of upper engaging section 38 moves in response to movement of the lower support member 19, and thus provides a polycentric hinge for the temporomandibular joint. The coil springs maintain the lower support member in relationship to the upper support member. The wires 122 resist the movement of the lower support member 14 so as to simulate the ligament of the jaw. However, the user is able to more freely move lower support member to simulate the actual movement of the lower jaw of a patient. The lower support member 14 can be moved in any direction permitted by the coil springs 62 and wires 122. Additionally, the condyle 19 moves such that outer surface 47, as it engages recess 41, simulates a human temporomandibular condylar joint, thus allowing the upper engaging surface 38 to ride on the area of fossae block member 48 which simulates the superior eminence. In the event engaging section 38 disengages from recess 41, it will be captured in capture recess 49 so that the user will not lose control of the device.

Referring to FIG. 7 there is illustrated how the lateral movement may occur to simulate lateral movement in a temporomandibular joint. In particular, the condyle 19 on the left-hand side (as seen by the viewer) leaves the corresponding fossae recess in fossae block member. The block member 128 associated with wire 122 secured to the condyle support member 18 is moved so that the block rests against the top surface, whereas the condyle on the right-hand side is moved only slightly. Thus it can be seen that lateral displacement of the lower support member cannot be effectuated beyond predetermined limits.

Figure 9A:
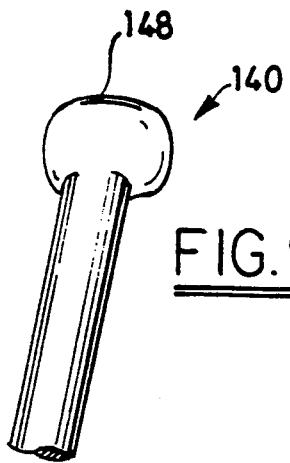
FIG. 9A is a front elevational view of a modified condyle made in accordance with the present invention which has been designed to have a configuration similar to that of a patient.
Figure 9B:
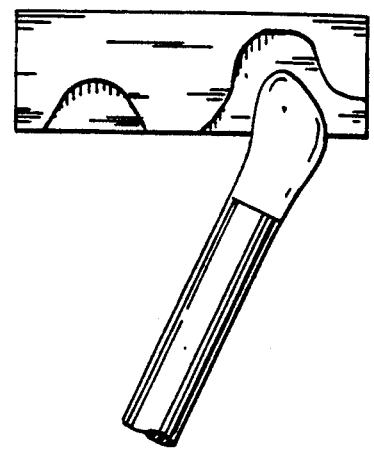
FIG. 9B is a side elevational view of the condyle of FIG. 9A illustrated in combination with an associated fossae block member, also designed to replicate the actual configuration of a temporomandibular joint of a patient.
Figure 9C:
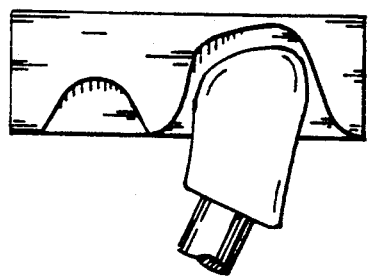
FIGS. 9C-9E illustrate alternative configurations of condyle members and associated fossae block members designed to replicate various configurations of temporomandibular joints in patients.
Figure 9D:
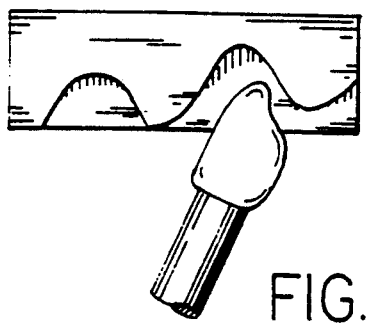
Figure 9E:
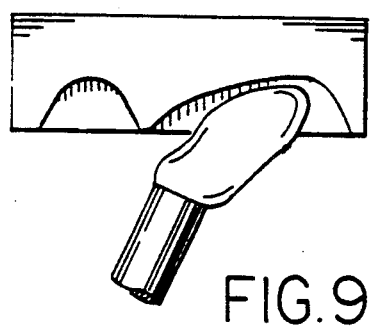
Figure 10:
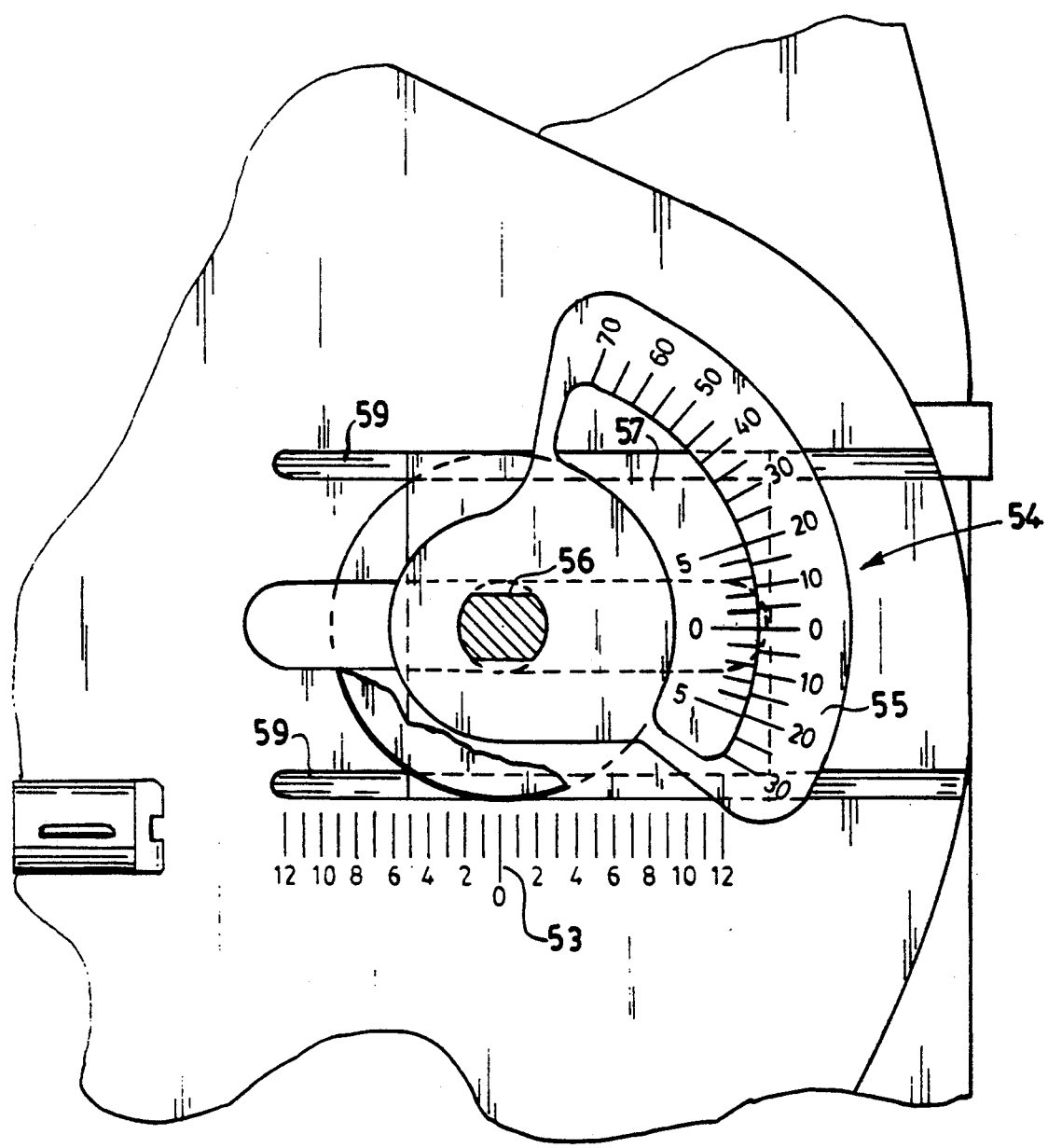
FIG. 10 is an enlarged partial top plan view of FIG. 3 illustrating the means used to secure and orient each fossae block member in the articulator.
Figure 11:
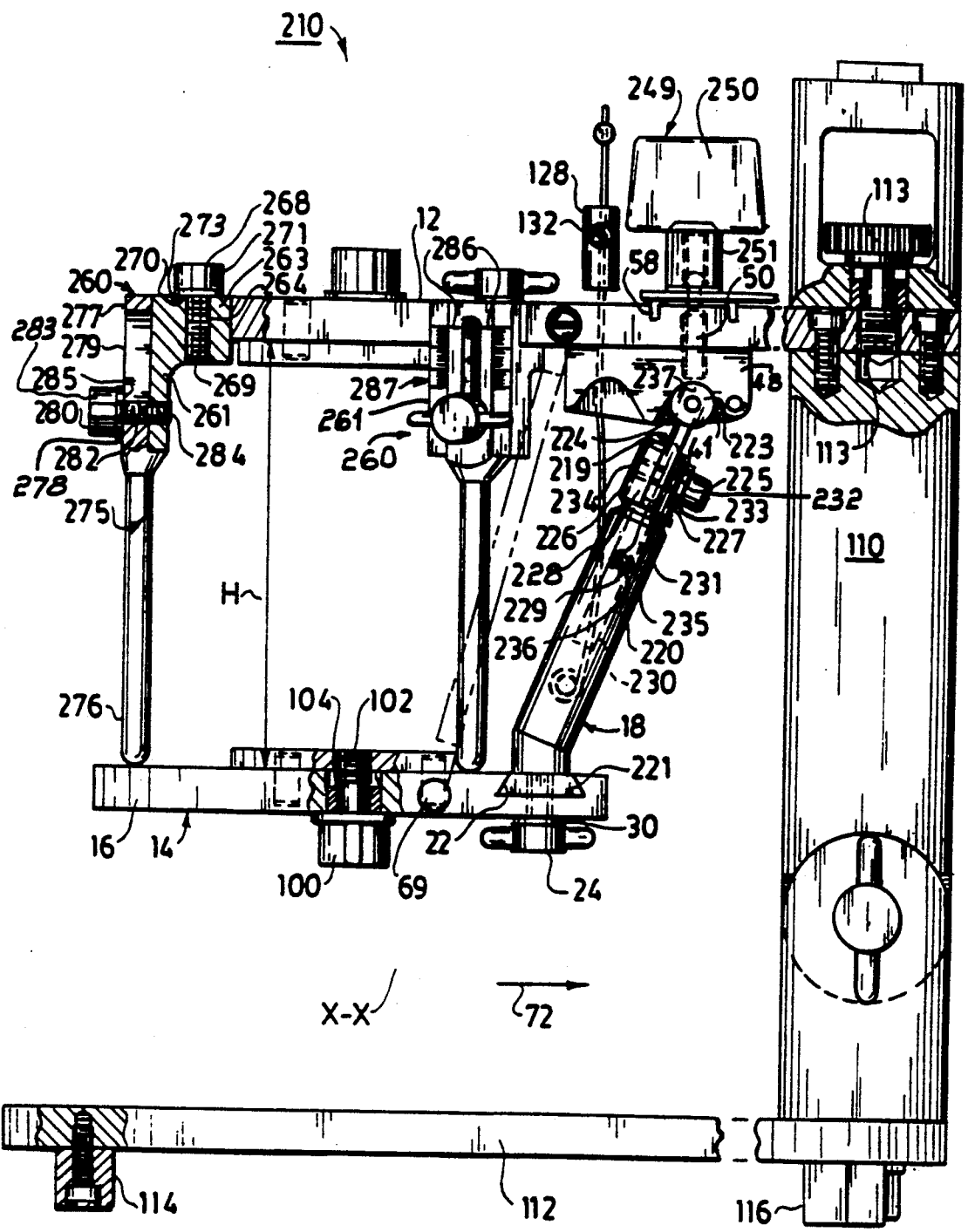
FIG. 11 is a side elevational view of a modified articulator made in accordance with the present invention.

Referring to FIG. 9A, there is illustrated a front elevational view of a modified condyle 140 made also in accordance with the present invention. In this particular embodiment outer engagement surface 148 is substantially round as viewed in the frontal view and has a cross-sectional configuration as illustrated in FIG. 9B. These shaped configurations more closely resemble actual condyle temporomandibular joints as they exist in patients. By simply modifying the configuration of the condyle 19, more accurate movement of the lower jaw may be had as it closely resembles that actually occurring in the patient. FIGS. 9C, 9D and 9E illustrate various other configurations that condyle 19 and fossae recess 40 may take. It is of course to be understood that the configuration of the condyle may be varied to any shape desired.

Referring to FIGS. 11-17, there is illustrated a modified articulator 210 also made in accordance with the present invention. The articulator 210 is similar to the articulator 10, with like numerals indicating like parts. This modified embodiment provides means to make it easier to use and more closely replicate the jaw of the patient. In all other respects, the articulator 210 operates and functions in the same manner as articulator 10.

As with articulator 10, articulator 210 includes an upper member 12 supporting a first dental cast (not shown) and a lower support member 14 supporting a second dental cast (not shown). The lower support member comprises a base member 16 which supports the second dental cast and a pair of axially spaced condyle support member 18. Each condyle support member includes a condyle assembly 219 and a mounting section 220. The lower end 221 is an integral portion of mounting section 220 and is designed to slide within axially extending slot 22 provided in base member 16. This is in contrast to the embodiment illustrated in FIGS. 1-10 wherein support member 18 comprises a support section 20 having a lower mounting end 21 pivotably secured thereto. It has been found that a single integral mounting section 220 provides adequate movement of the lower base member 16 and avoids any undesired movement.

The condyle assembly 219 includes a condyle 223 having an outer engagement surface 224 and a mounting projection 225 extending therefrom. In the particular embodiment illustrated, mounting projection 225 comprises a generally U-shaped configuration with the leg portions secured to outer engagement surface 224. In the embodiment illustrated, outer engagement surface 224 is substantially cylindrical in shape. The condyle assembly 219 further includes a mounting member 226 which comprises a pair of condyle clamping section 227, 228 spaced apart by a recess 229 designed to receive mounting projection 225. The mounting member 226 further comprises a generally cylindrical shaft 230 designed to engage a mating cylindrical recess 231 provided in the lower condyle section 220. A sufficient amount of clearance is provided between shaft 230 and recess 231 to allow shaft 230 to rotate about its longitudinal axis. The mounting projection 225 is securely held in position in recess 229 by a threaded screw 232 which passes through an opening 233 in clamping section 227, through the leg portions of U-shaped projection 225 and into a threaded opening 234 in section 228. As screw 232 is tightened, the two clamping sections 227, 228 are caused to clampingly engage mounting projection 225 therebetween. A set screw 235 is provided in a threaded opening 236 in lower mounting section 220 which extends through to recess 231 such that it engages the outer surface of shaft 229. This allows the condyle assembly 219 to be moved along its longitudinal axis, extended or retracted from mounting section 220, and locked at any desired position.

Figure 12:
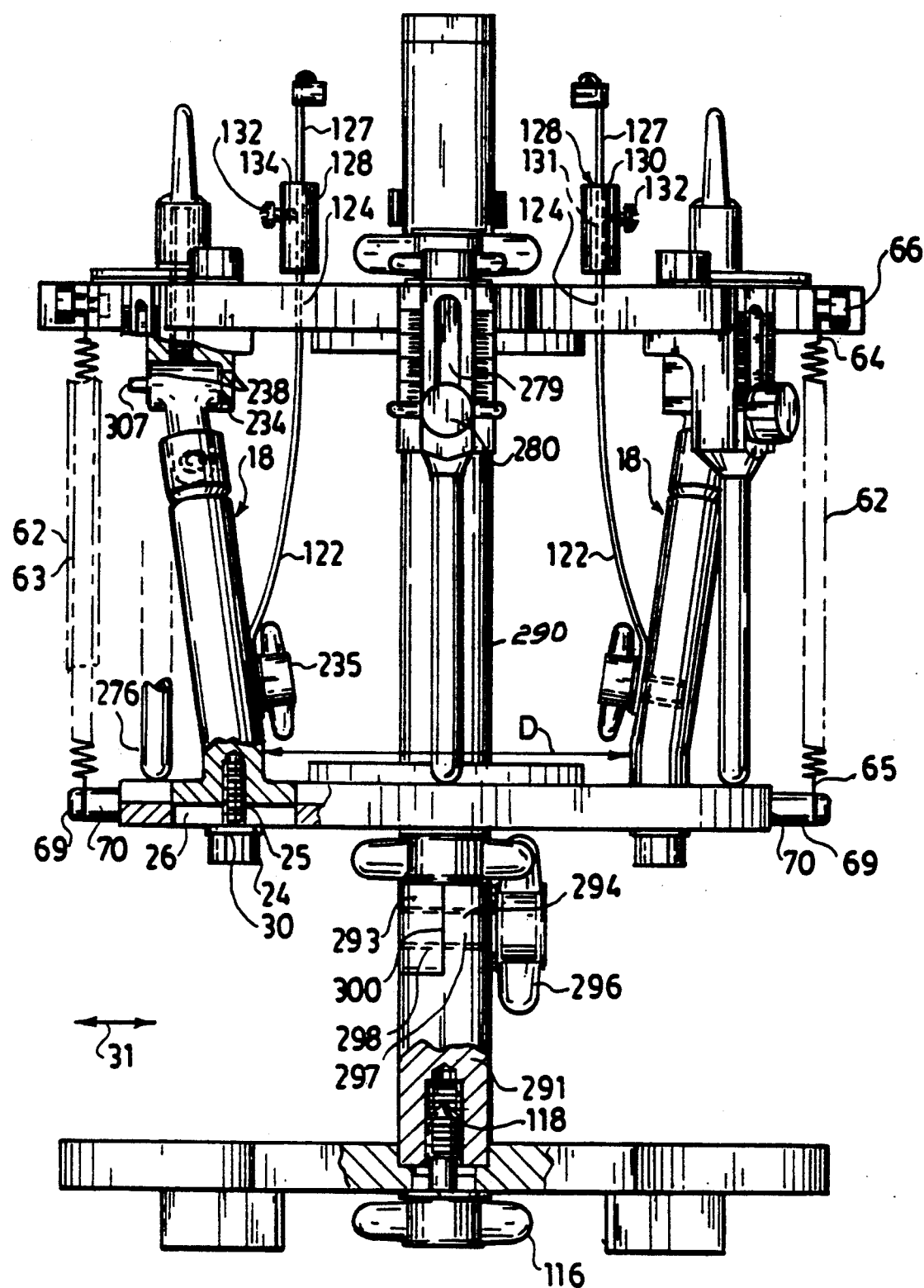
FIG. 12 is a front elevational view, 11; partially broken away, of the articulator of FIG.

In this embodiment, fossae member 48 is mounted to the upper member 12 to allow movement of the condyle 223 such that condyle 223 and fossae member 48 may be adjusted to a variety of positions to replicate the patient's jaw structure. The point about which the fossae member 48 is rotated has been located such that the center line 237 of outer engagement section 224 and fossae recess 41 coincide as best seen in FIG. 12. Preferably, also as illustrated in FIG. 12, the pivot point is substantially midway between the sides 238 of condyle 223. Thus the condyle 223 and fossae recess 41 can both be manipulated along at least two axes so that condyle 223 properly seats within recess 41 to allow proper movement therebetween.

Figure 13:
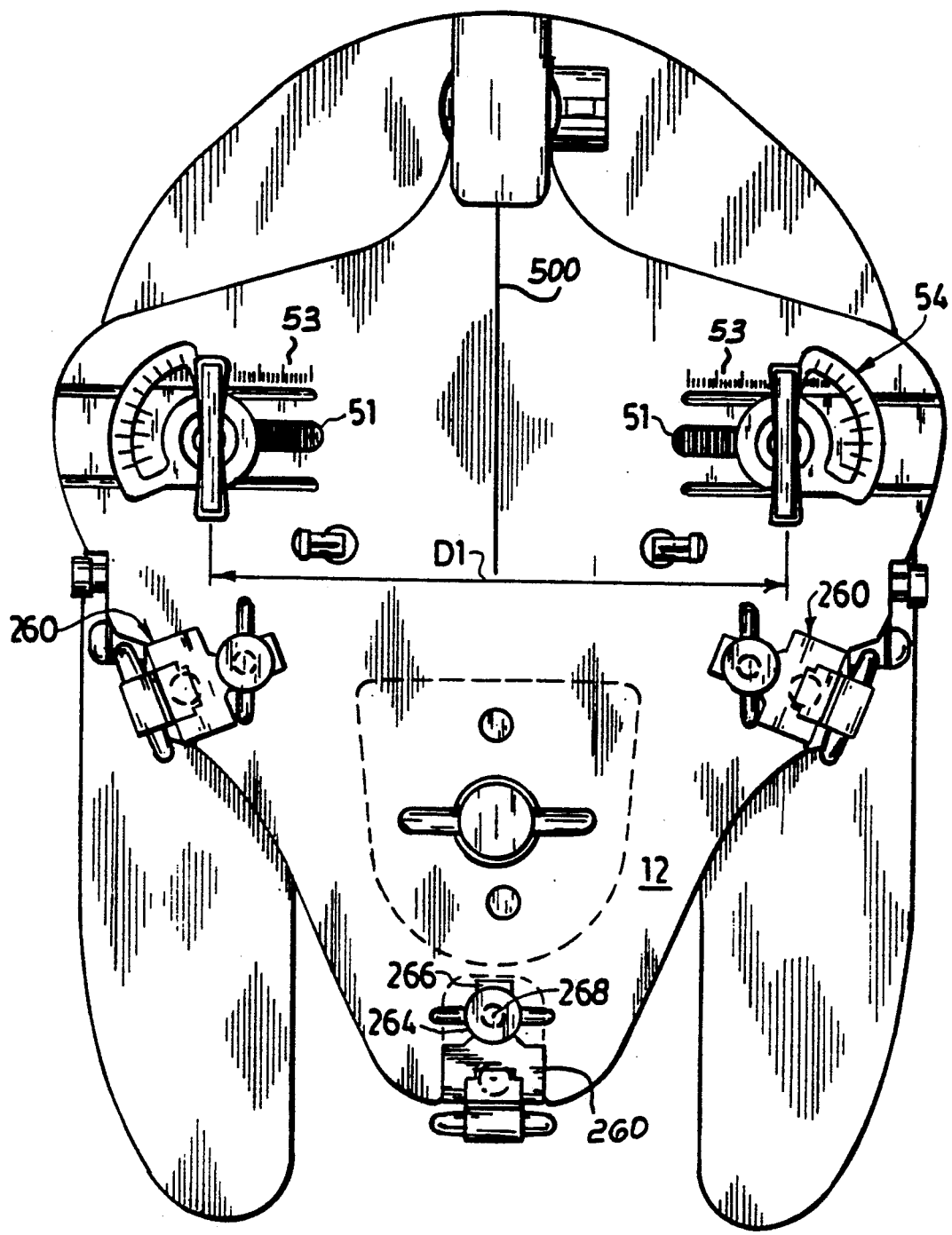
FIG. 13 is a top plan view of the articulator of FIG. 11.
Figure 14:
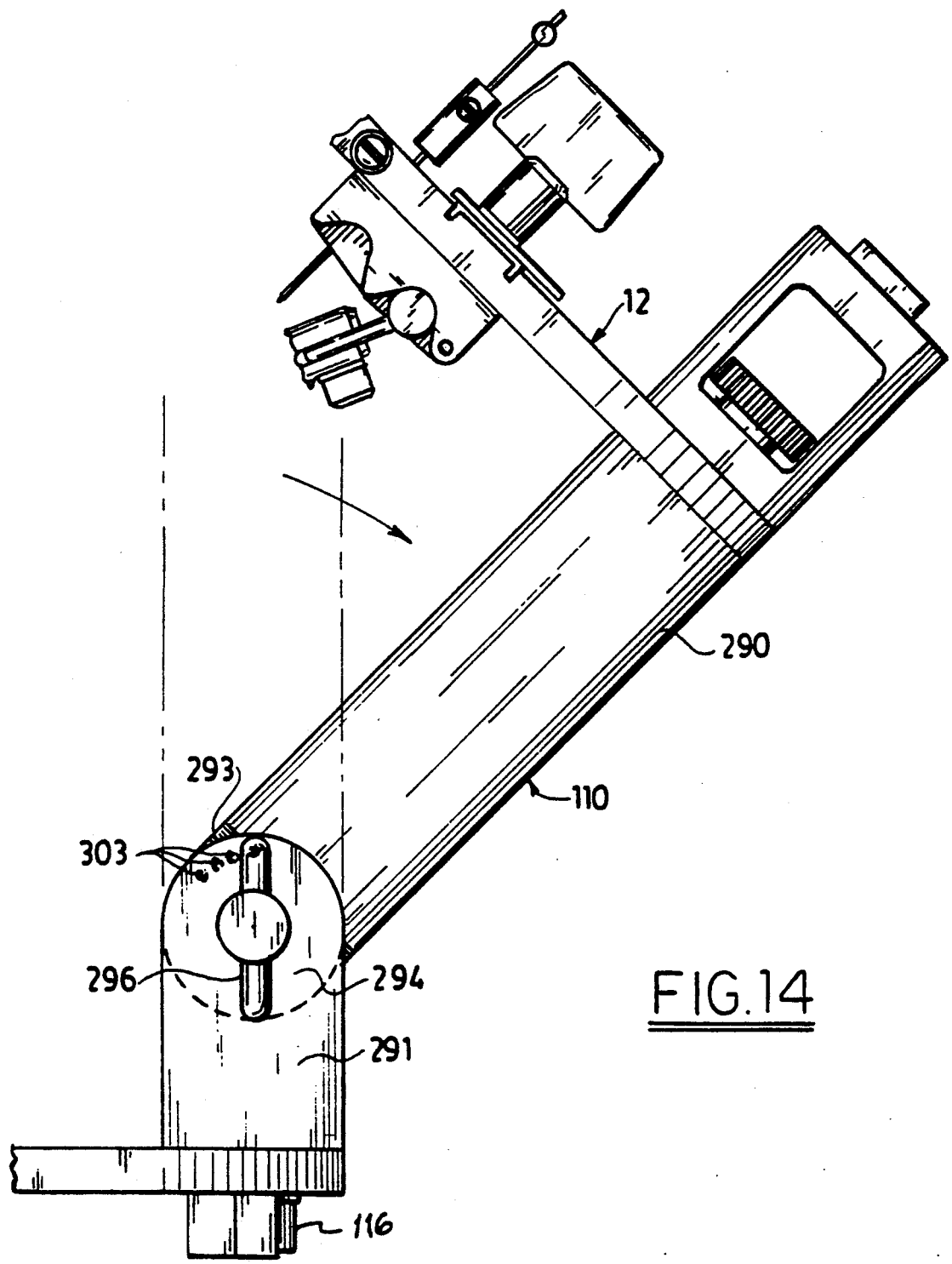
FIG. 14 is an enlarged partial view of one embodiment of the neck support portion of the articulator of FIG. 11.

With reference to FIG. 13, the upper surface of upper support member 12 has a centerline 500 scribed therein. Centerline 500 represents the foramen magnum of a patient and facilitates the placement or location of the fossae members 48, thereby more accurately replicating the anatomical structure of the patient.

In order to make it easier for the user to move fossae block 48 a wing head knob 249 is provided. The wing head knob 249 comprises an upper finger clamping section 250 having a generally planar configuration and an integrally formed lower connecting portion 251 which is designed to receive the upper end of the shaft 50 in a non twisting manner. As knob 249 is loosened, fossae block 48 can be easily rotated about shaft 50. When the fossae block 48 is positioned at the desired location, knob 249 is tightened so as to lock fossae block 48 in position.

Figure 15:
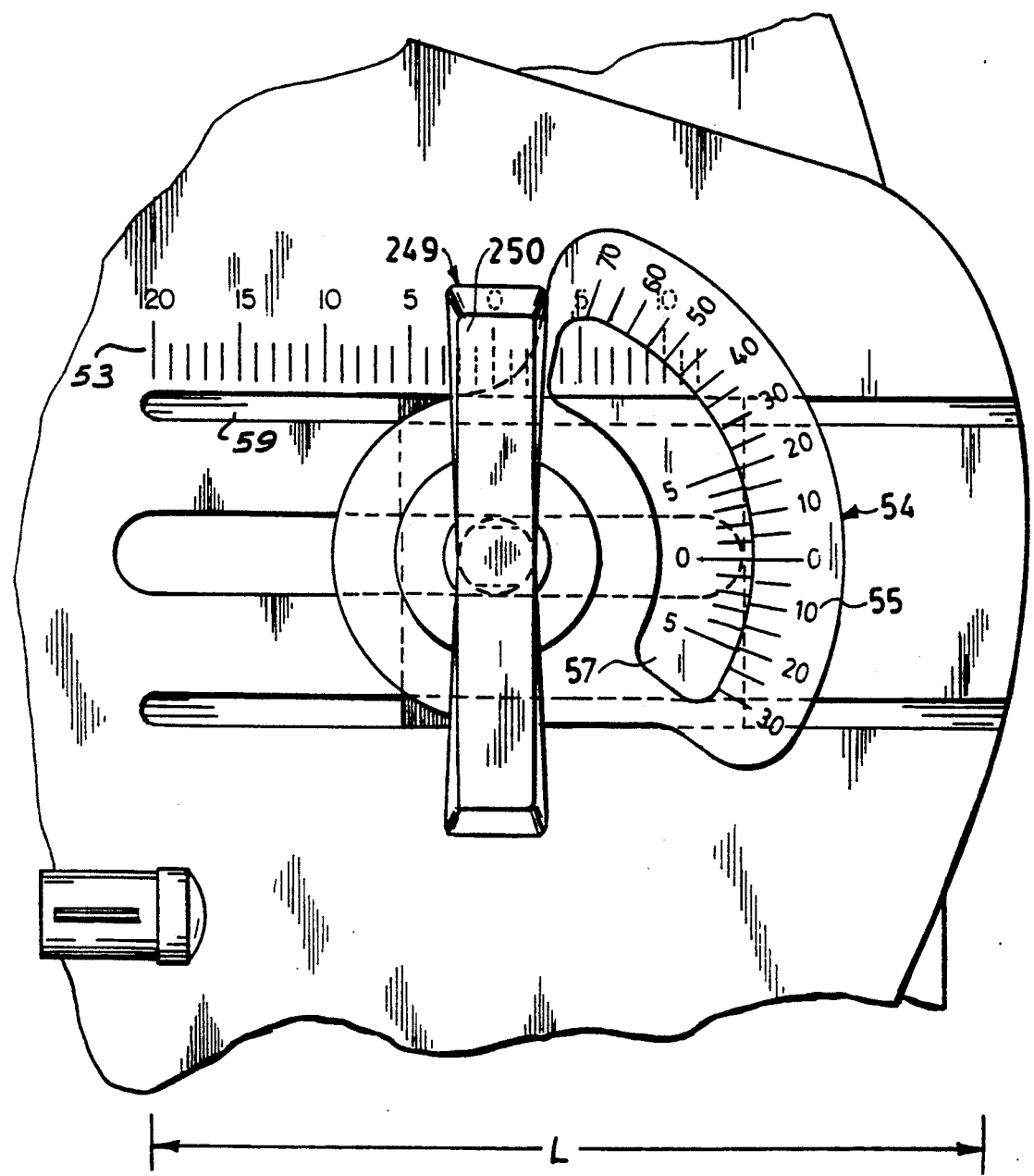
FIG. 15 is an enlarged partial top plan view of FIG. 13 illustrating the means used to secure and orient each fossae block member in the articulator.

Referring to FIG. 15, there is illustrated an enlarged partial top view of the articulator 210 (similar to FIG. 10), like numerals indicating like parts. The only substantial difference, other than the configuration of the knob 249 previously discussed, is that the recesses 59 have been made longer in the dimension denoted L in FIG. 15 in order to permit a wider range of movement to accommodate both adult and child sized models. The mounting means is still used in the same manner previously discussed in the embodiment of FIGS. 1-10.

In this modified embodiment, means are also provided to allow clear and free access to the dental models while at the same time allowing the base member 16 to be easily repositioned with respect to the upper support member 12. In the embodiment of FIGS. 1-10, a scale is provided on the rods 80 to record the desired spacing between upper and lower member 12,14 before removal of the rods 80. In the modified embodiment of FIGS. 11-17, the need to record and recalibrate the rods with respect to the upper member 12 is eliminated. In order to accomplish this, removable post assemblies 260 are provided at each location where rods 80, 92 were previously provided in the earlier-described embodiment. Removable post assemblies 260 are designed to be releasably mounted with respect to upper support member 12.

In the particular embodiment illustrated, each post assembly 260 (of which there are three shown) comprises an anchor member 261, which has a generally L-shaped cross-section which includes an upper engagement section 263 designed to be received in a mating recess 266 provided in upper support member 12. A threaded wing head screw 268 secures the anchor post assembly 260 to the upper support member 12. The threaded shaft 264 of wing head screw 268 engages a threaded opening 269 in anchor member 261. When the wing head screw 268 is tightened, the engaging surface 270 of the head 271 of the wing head screw 268 engages the top surface of upper support member 12 as indicated by numeral 273. By appropriately tightening or loosening wing head screw 268, the anchor post assembly 260 can either be placed on or removed from upper support member 12. When wing head screw 268 is firmly tightened, the anchor post assembly 260 will always be placed in the same position with respect to upper support member 12. If desired, each of the post assemblies may be identified for use at a particular location. For example, each post assembly may be identified with a letter, A, B, C, etc., and the corresponding position at which the post assembly is to be placed is identified with a corresponding reference character.

Each anchor post assembly 260 includes a moveable post member 275 having a lower end 276 designed to engage the top surface of lower member 16, and an upper end 277 designed to slide within a mating recess 278 in anchor member 261. Upper end 277 has an elongated slot 279 through which a threaded winged head screw 280 extends. The screw 280 has a threaded shank 282 which engages a threaded opening 284 in anchor member 261. As screw 280 is tightened, the inner surface 285 of the head 283 of wing screw 280 engages the area of the post member 275 adjacent thereto, resulting in clamping the post member 275 to the anchor member 261 in a desired position. As the screw 280 is loosened, the post member 275 may be moved vertically up or down with respect to anchor member 261. In the particular embodiment illustrated, the outer surface of the post member 275 is provided with a marking line 286 which is designed to align with a scale 287 on anchor member 261. As the post member 275 is moved up or down, an accurate reading may be obtained as to the relative position of post member 275 with respect to lower support member 14.

Once the user has appropriately locked the positions of the post member 275 for each of the post assemblies 260, the user may remove the post assemblies 260 to allow full and free access to the models. Later, should the user desire to go back to the original position, the user need only place the post assemblies 260 back in their respective original positions to replicate the original orientation of the support members. In this manner, there is no need to disturb the accurate placement of the post members 275 with respect to the lower support member 14.

In the embodiment illustrated, the lower support member 14 no longer is provided with recesses for receiving of the terminal end of each post member 275. This avoids the necessity of properly aligning the post member 275 with respect to such recess. In this embodiment, the post member 275 need only engage the upper surface of the lower support member 14.

In this embodiment, means are also provided to allow readjustability of the neck portion 110 so that the user can more easily work with the models held in the articulator. It has been found that under certain conditions, the user may be working on a model located in an inconvenient or difficult position. In this regard, neck portion 110 has been designed to be adjustable to a variety of angled positions to make it easier for the technician to work on the model. In particular, neck portion 110 consists of an upper section 290 and a lower section 291, which are pivotable with respect to one another. Lower section 291 is secured to base 112 by wing head screw 116. In the embodiment shown in FIG. 14, upper section 290 has an engagement flange 293 designed to be placed adjacent and engage flange member 294 of lower section 291. Means are provided to clampingly engaging the upper and lower flanges 293, 294 together at any desired rotational position. In the particular embodiment illustrated this is accomplished by providing a threaded wing head screw 296 which has threaded shaft 297 that engages threaded opening 298 in flange 293. Thus, as the wing head screw 296 is tightened, the two flanges 293, 294 engage one another and are locked in the desired relative position.

In the preferred embodiment illustrated, a projection 300 is provided on the mating surface of flange 294 which is designed to mate into one of several corresponding spaced recesses 303 in the flange 293. As the upper section 290 is rotated (preferably up to a maximum of about 45° with respect to lower section 291), the projection 300 engages one of the respective recesses 303 to assist in locating the upper section 290 into one of several predetermined orientations with respect to lower section 291 In the preferred embodiment illustrated, the projection 300 and plurality of recesses 303 are designed to provide orientation of the upper section 290 at 0°, 15°, 30° and 45° with respect to lower section 291.

Figure 16:
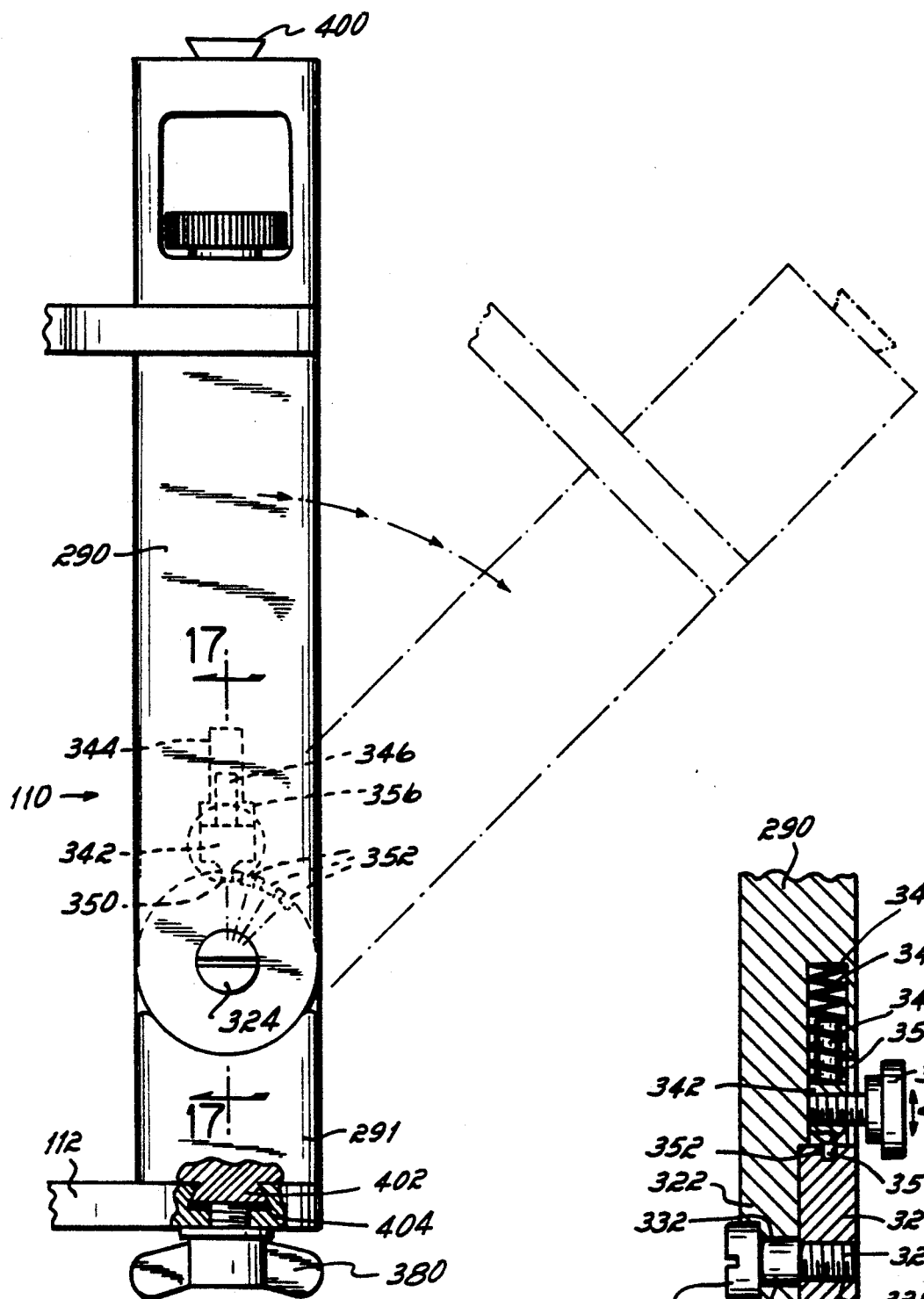
FIG. 16 is an enlarged partial view of an alternative embodiment of the neck support portion of the articulator of FIG. 11, and shows a second position in phantom.
Figure 17:
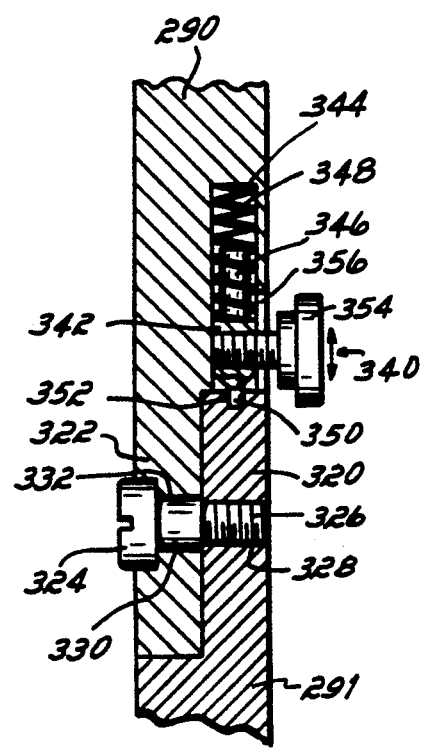
FIG. 17 is a cross-sectional view of a portion of the neck support portion taken on line 17—17 of FIG. 16.

An alternative embodiment of neck portion 110 is shown in FIGS. 16 and 17. As shown, lower section 291 has an engagement flange 320 and upper section 290 has an engagement flange 322. Flanges 320, 322 are secured in pivotable, abutting relation to one another, as shown clearly in FIG. 17, by means of pivot screw 324. The screw 324 has a threaded shaft portion 326 which engages a threaded opening 328 in flange 320, and an unthreaded shaft portion 330 which passes through an unthreaded opening 332 in flange 322. Thus, pivot screw 324 secures flanges 320, 322 in abutting relation, but permits them (and thereby upper and lower sections 290, 291) to be pivoted with respect to one another about the unthreaded shaft portion 330.

Neck portion 110 of this embodiment is further provided with means for retaining the upper and lower sections 290, 291 thereof in a desired pivotal orientation with respect to one another, as shown in FIGS. 16 and 17. The retaining means 340 shown comprises a chuck 342 slidably received in recess 344 in upper section 290. Chuck 342 has an upwardly extending pin 346 which is received by coil spring 348 and a downwardly extending pin 350 which engages tooth-like notches 352 in flange 320. Spring 348 is captured in recess 344 and provides sufficient force (generally downwardly) on chuck 342 to maintain the engagement pin 350 in a notch 352, thereby fixing upper and lower sections 290, 291, respectively, in a desired pivotal orientation. Chuck 342 is manipulated in the directions of the arrows by means of knob 354 which is threadably received by chuck 342 through slot 356 in upper member 290. By grasping knob 354, a user can disengage pin 350 from a notch 352, pivotally re-orient the upper and lower sections 290, 291 with respect to one another, and re-engage pin 350 in a different notch 352 to thereby lock the upper and lower sections in the selected pivotal orientation. This structure provides easy manipulation and orientation of the neck portion.

As shown in FIG. 16, neck portion 110 has male dovetail members 400 and 402 at the ends of its upper and lower sections 290, 291, respectively, to secure neck portion 110 to base 112. Dovetail members 400, 402 are designed to engage in female dovetail slot 404 in base 112. Thus, neck portion 110 can be inverted from the position shown in FIG. 16 so that male dovetail member 400 is engaged in slot 404 to facilitate a different orientation of and access to a dental model mounted in the articulator device. Once a male dovetail member (400 or 402) is engaged in female slot 404, wing screw 380 is tightened to retain neck portion 110 in the desired position.

In the preferred embodiment illustrated, it has been found that the size of block 130, which rides on flexible connecting element 122, should be of a size to allow easy manipulation by the user. In the particular embodiment illustrated, block 130 has a length of about ¾ of an inch. However, it is to be understood that this may be varied as appropriately desired.

It has also been found desirable to replace various circular knobs shown in the embodiment of FIGS. 1–10 with wing shaped knobs to make it easier for the user to engage or disengage by hand the associated elements. For example, the lower end 126 of wire 122 is secured to condyle 18 by wing head screw 235 to allow easier securing or removal by hand.

To further provide versatility to articulator 210, condyles 223 are each provided with an axially extending pin 307 that may be used to attach a face bow and/or a bite plate used to set models in proper occlusion. Thereby providing additional means to replicate a patient's occlusion.

It is to be understood that various other changes and modifications may be made without departing from the spirit or scope of the present invention as defined by the appended claims.

What is claimed is:

1. A dental articulator comprising:
   an upper support member for supporting a first dental cast;
   a lower support member having a base member for supporting a second dental cast;
   joint means for simulating the mandibular condylar joint and for mounting said lower support member to said upper support member;
   means for simulating the ligaments of a patient which secure the lower jaw to the upper jaw, said means for simulating the ligaments of a patient comprising a pair of flexible connecting elements, one of said flexible connecting elements associated with each of said condyle support members, each of said flexible elements having a lower end and an upper end, said lower end being secured to its associated condyle support member, said upper end being secured to said upper support member.

2. A dental articulator according to claim 1 wherein said upper end extends through an opening in said upper support member and has means for adjusting the degree of movement of said lower support member with respect to said upper support member.

3. A dental articulator according to claim 2 wherein said means for adjusting the degree of movement comprises a block having a hole through which said upper end of said flexible element extends and a set screw for adjusting and securing the position of said block along the upper end of said element, said block designed to bear against the upper surface of said upper support member.

4. A dental articulator according to claim 1 further comprising
   means for positioning said lower support member with respect to said upper support member a desired distance comprising at least one removable post assembly having an anchor member, means for releasably mounting and dismounting said anchor member, a post member slidably mounted to said anchor member, and means for securely positioning said post member with respect to said anchor member at any desired position.

5. A dental articulator according to claim 4 wherein said means for releasably mounting and dismounting said anchor member comprises a screw having a threaded shank which engages a threaded opening in said anchor member, said screw having a configuration such that when it is threaded into engagement with said anchor member it bears against said upper support member to lock said anchor assembly in place.

6. A dental articulator according to claim 5 wherein said means for securely positioning said post member to said anchor member comprises a screw which has a threaded shank which extends through an opening in said post member and engages a threaded opening in said anchor member.

7. A dental articulator comprising:
   an upper support member for supporting a first dental cast;
   a lower support member having a base member for supporting a second dental cast;
   joint means for simulating the mandibular condylar joint and for mounting said lower support member to said upper support member;
   a neck portion secured at the rearward end of said upper support member, said neck portion having an upper section and a lower section, said upper section has a lower end which is designed to mate and rotatably engage an upper end portion of said lower section;
   a base portion secured to the lower section of said neck portion, said neck portion having a length such that said lower support member is spaced from said base portion; and
   means for adjusting the angular position of said upper section of said neck portion with respect to said lower section of said neck portion, siad means including locating means to assist in locating and locking said upper and lower sections at a particular angular relationship.

8. A dental articulator according to claim 7 wherein said neck portion further includes a male dovetail member at the upper end of said upper section and at the lower end of said lower section, and wherein said base portion includes a female dovetail slot for receiving and engaging one of said male dovetail members.

* * * * *